United States Patent
Trese et al.

(10) Patent No.: US 10,799,557 B2
(45) Date of Patent: Oct. 13, 2020

(54) NORRIN REGULATION OF JUNCTION PROTEINS AND THE USE THEREOF TO TREAT EPITHELIAL OR ENDOTHELIAL MEMBRANE LEAKAGE INDUCED EDEMA

(71) Applicant: RETINAL SOLUTIONS LLC, Ann Arbor, MI (US)

(72) Inventors: Michael T. Trese, Novi, MI (US);
Antonio Capone, Novi, MI (US);
Kimberly Drenser, Novi, MI (US)

(73) Assignee: RETINAL SOLUTIONS LLC, Ann Arbor, MI (US)

( * ) Notice: Subject to any disclaimer, the term of this patent is extended or adjusted under 35 U.S.C. 154(b) by 0 days.

(21) Appl. No.: 16/218,016

(22) Filed: Dec. 12, 2018

(65) Prior Publication Data

US 2019/0105372 A1 Apr. 11, 2019

Related U.S. Application Data

(63) Continuation of application No. 14/733,876, filed on Jun. 8, 2015, now Pat. No. 10,206,978.

(51) Int. Cl.
| | |
|---|---|
| *A61K 38/18* | (2006.01) |
| *A61P 7/10* | (2006.01) |
| *A61P 29/00* | (2006.01) |
| *A61P 1/00* | (2006.01) |
| *A61P 9/10* | (2006.01) |
| *A61P 9/14* | (2006.01) |
| *A61K 39/395* | (2006.01) |
| *A61K 38/17* | (2006.01) |
| *C07K 14/475* | (2006.01) |
| *C07K 14/515* | (2006.01) |
| *C07K 16/22* | (2006.01) |

(52) U.S. Cl.
CPC ...... *A61K 38/1709* (2013.01); *A61K 38/1891* (2013.01); *A61P 1/00* (2018.01); *A61P 7/10* (2018.01); *A61P 9/10* (2018.01); *A61P 9/14* (2018.01); *A61P 29/00* (2018.01); *C07K 14/475* (2013.01); *C07K 14/515* (2013.01); *C07K 16/22* (2013.01)

(58) Field of Classification Search
None
See application file for complete search history.

(56) References Cited

U.S. PATENT DOCUMENTS

| | | |
|---|---|---|
| 4,588,585 A | 5/1986 | Mark et al. |
| 5,378,475 A | 1/1995 | Smith et al. |
| 5,773,019 A | 6/1998 | Ashton et al. |
| 6,001,386 A | 12/1999 | Ashton et al. |
| 6,217,895 B1 | 4/2001 | Guo et al. |
| 6,375,972 B1 | 4/2002 | Guo et al. |
| 6,756,058 B2 | 6/2004 | Brubaker et al. |
| 9,114,078 B2 | 8/2015 | Drenser |
| 2004/0054374 A1 | 3/2004 | Weber et al. |
| 2005/0281861 A1 | 12/2005 | Hughes et al. |
| 2010/0129375 A1 | 5/2010 | Junge et al. |
| 2010/0239499 A1 | 9/2010 | Drenser |
| 2014/0171356 A1 | 6/2014 | Habib et al. |

FOREIGN PATENT DOCUMENTS

| | | |
|---|---|---|
| JP | 2003524381 A | 8/2003 |
| WO | 2009114878 A2 | 9/2009 |
| WO | 2014130728 A1 | 8/2014 |
| WO | 2014143022 A1 | 9/2014 |

OTHER PUBLICATIONS

Mark, D.F. et al., "Site-specific mutagenesis of the human fibroblast interferon gene", Proceedings of the National Academy of Sciences, Sep. 1984, pp. 5662-5666, vol. 81.

Meindl, A. et al., "Norrie disease is caused by mutations in an extracellular protein resembling C-terminal globular domain of mucins", Nature Genetics, Oct. 1992, pp. 139-143, vol. 2, © 1992 Nature Publishing Group.

Berger, W. et al., "Mutations in the candidate gene for Norrie disease", Human Molecular Genetics, 1992, pp. 461-465, vol. 1, No. 7, © Oxford University Press.

Chen, Z-Y. et al., "A mutation in the Norrie disease gene (NDP) associated with X-linked familial exudative vitreoretinopathy", Nature Genetics, Oct. 1993, pp. 180-183, vol. 5, © 1993 Nature Publishing Group.

McDonald, N.Q. et al., "A Structural Superfamily of Growth Factors Containing a Cystine Knot Motif", Cell, May 7, 1993, pp. 421-424, vol. 73, © 1993 by Cell Press.

Meitinger, T. et al., "Molecular Modeling of the Norrie Disease Protein Predicts a Cystine Knot Growth Factor Tertiary Structure", Nature Genetics, Dec. 1993, pp. 376-380, vol. 5.

Black, G. et al., "The Molecular Biology of Norrie's Disease", Eye, 1994, pp. 491-496, vol. 8, © 1994 Royal College of Ophthalmologists.

Schuback, D.E. et al., "Mutations in the Norrie Disease Gene", Human Mutation, 1995, pp. 285-292, vol. 5, © 1995 Wiley-Liss, Inc.

(Continued)

*Primary Examiner* — Zachary C Howard
(74) *Attorney, Agent, or Firm* — Blue Filament Law PLLC

(57) ABSTRACT

A method of tightening inter-cellular junctions in endothelial or epithelial cells includes exposing the endothelial or epithelial cells to a norrin in concert with an anti-VEGF agent. Upon sufficient contact time, for norrin to selectively up-regulate gene expression of Cadherin or claudin-5 in the endothelial or epithelial cells, the inter-cellular junctions are tightened.

14 Claims, 5 Drawing Sheets
Specification includes a Sequence Listing.

(56) References Cited

OTHER PUBLICATIONS

Shastry, B.S. et al., "Linkage and Candidate Gene Analysis of X-Linked Familial Exudative Vitreoretinopathy", Genomics, 1995, pp. 341-344, vol. 27, © 1995 by Academic Press, Inc.

Berger, W. et al., "An animal model for Norrie disease (ND): gene targeting of the mouse ND gene", Human Molecular Genetics, 1996, pp. 51-59, vol. 5, No. 1, © 1996 Oxford University Press.

Perez-Vilar, J. et al., "Norrie Disease Protein (Norrin) Forms Disulfide-linked Oligomers Associated with the Extracellular Matrix", The Journal of Biological Chemistry, Dec. 26, 1997, pp. 33410-33415, vol. 272, No. 52, © 1997 by The American Society for Biochemistry and Molecular Biology, Inc.

Willert, K. et al., "β-catenin: a key mediator of Wnt signaling", Current Opinion in Genetics & Development, 1998, pp. 95-102, vol. 8, © Current Biology Ltd.

Berger, W., "Molecular Dissection of Norrie Disease", Acta Anatomica, 1998, pp. 95-100, vol. 162, © 1998 S. Karger AG.

Black, G.C.M. et al., "Coats' disease of the retina (unilateral retinal telangiectasis) caused by somatic mutation in the NDP gene: a role for norrin in retinal angiogenesis", Human Molecular Genetics, 1999, pp. 2031-2035, vol. 8, No. 11, © 1999 Oxford University Press.

Talks, S. J. et al., "De novo mutations in the 5' regulatory region of the Norrie disease gene in retinopathy of prematurity", Journal of Medical Genetics, 2001, pp. 1-6, vol. 38:e46.

Hiraoka, M. et al., "Insertion and deletion mutations in the dinucleotide repeat region of the Norrie disease gene in patients with advanced retinopathy of prematurity", Journal of Human Genetics, 2001, pp. 178-181, vol. 46, © 2001 Jpn Soc Hum Genet and Springer-Verlag.

Robitaille, J. et al., "Mutant frizzled-4 disrupts retinal angiogenesis in familial exudative vitreoretinopathy", Nature Genetics, Sep. 2002 (Published online: Aug. 12, 2002), pp. 326-330, vol. 32, © 2002 Nature Publishing Group; DOI: 10.1038/ng957.

Fu, K. et al, "A Potential Approach for Decreasing the Burst Effect of Protein from PLGA Microspheres", Journal of Pharmaceutical Sciences, Aug. 2003, pp. 1582-1591, vol. 92, No. 8, © 2003 Wiley-Liss, Inc. and the American Pharmacists Association.

Xu, Q. et al., "Vascular Development in the Retina and Inner Ear: Control by Norrin and Frizzled-4, a High-Affinity Ligand-Receptor Pair", Cell, Mar. 19, 2004, pp. 883-895, vol. 116, © 2004 by Cell Press.

Clevers, H., "Wnt Signaling: Ig-Norrin the Dogma", Current Biology, Jun. 8, 2004, pp. R436-R437, vol. 14, © 2004 Elsevier Ltd.; DOI: 10.1016/j.cub.2004.05.039.

Niehrs, C., "Norrin and Frizzled: A New Vein for the Eye", Developmental Cell, Apr. 2004, pp. 453-461, vol. 6, © 2004 by Cell Press.

Yao, R. et al., "MAGI-3 is involved in the regulation of the JNK signaling pathway as a scaffold protein for frizzled and Ltap", Oncogene, 2004, pp. 6023-6030, vol. 23, © 2004 Nature Publishing Group; DOI: 10.1038/sj.onc.1207817.

Hutcheson, K.A. et al., "Norrie disease gene sequence variants in an ethnically diverse population with retinopathy of prematurity", Molecular Vision, Jul. 14, 2005, pp. 501-508, vol. 11, © 2005 Molecular Vision.

Hines, L. et al., "Norrie disease pseudoglioma protein, partial [synthetic construct]", NCBI, 2005, 2 pages, GenBank accession No. AAX29917.1.

Gavard, J. et al., "VEGF controls endothelial-cell permeability by promoting the β-arrestin-dependent endocytosis of VE-cadherin", Nature Cell Biology, Nov. 2006, pp. 1223-1234, vol. 8, No. 11, © 2006 Nature Publishing Group; DOI: 10.1038/ncb1486.

Groten, T. et al., "Cell junctional proteins in the human corpus luteum: changes during the normal cycle and after HCG treatment", Human Reproduction, 2006 (Advance Access publication Aug. 21, 2006), pp. 3096-3102, vol. 21, No. 12, © 2006 The Authors; DOI: 10.1093/humrep/del286.

Smallwood, P.M. et al., "Mutational Analysis of Norrin-Frizzled4 Recognition", The Journal of Biological Chemistry, Feb. 9, 2007, pp. 4057-4068, vol. 282, No. 6, © 2007 The American Society for Biochemistry and Molecular Biology, Inc.

Jiang, C. et al., "Intravitreal injections of GDNF-loaded biodegradable microspheres are neuroprotective in a rat model of glaucoma", Molecular Vision, Sep. 24, 2007, pp. 1783-1792, vol. 13, © 2007 Molecular Vision.

Taddei, A. et al., "Endothelial adherens junctions control tight junctions by VE-cadherin-mediated upregulation of claudin-5", Nature Cell Biology, Aug. 2008, pp. 923-934, vol. 10, No. 8, © 2008 Macmillan Publishers Limited; DOI: 10.1038/ncb1752.

Schulzke, J. D. et al., "Epithelial Tight Junctions in Intestinal Inflammation", Molecular Structure and Function of the Tight Junction: Ann. N.Y. Acad. Sci., May 2009, pp. 294-300, vol. 1165, © 2009 New York Academy of Sciences; DOI: 10.1111/j.1749-6632.2009.04062.x.

Ye, X. et al., "Norrin, Frizzled4, and Lrp5 signaling in endothelial cells controls a genetic program for retinal vascularization", Cell, Author Manuscript available in PMC Apr. 16, 2010, Published in final edited form on Oct. 16, 2009, pp. 285-298, vol. 139, No. 2; DOI: 10.1016/j.cell.2009.07.047.

Junge, H.J. et al., "TSPAN12 Regulates Retinal Vascular Development by Promoting Norrin- but Not Wnt-Induced FZD4/β-Catenin Signaling", Cell, Oct. 16, 2009, pp. 299-311, vol. 139, © 2009 Elsevier Inc; DOI: 10.1016/j.cell.2009.07.048.

Ohlmann, A. et al., "Norrin Promotes Vascular Regrowth after Oxygen-Induced Retinal Vessel Loss and Suppresses Retinopathy in Mice", Neurobiology of Disease, Jan. 6, 2010, pp. 183-193, vol. 30, No. 1, © 2010 The Authors; DOI:10.1523/JNEUROSCI.3210-09.2010.

Chakraborty, S. et al., "Lymphatic system acts as a vital link between metabolic syndrome and inflammation", Ann. N.Y. Acad. Sci., Author Manuscript available in PMC Oct. 1, 2011, Published in final edited form in Oct. 2010, pp. E94-E102, vol. 1207 (Suppl. 1); DOI: 10.1111/j.1749-6632.2010.05752.x.

National Eye Institute, Definition of Macular Edema, Apr. 5, 2010, 2 pages; https://www.nei.nih.gov/faqs/retina-macular-edema.

Paes, K.T. et al., "Frizzled 4 is Required for Retinal Angiogenesis and Maintenance of the Blood-Retina Barrier", Investigative Ophthalmology & Visual Science, Aug. 2011, pp. 6452-6461, vol. 52, No. 9, © 2011 The Association for Research in Vision and Ophthalmology, Inc.

Descamps, B. et al., "Frizzled 4 Regulates Arterial Network Organization Through Noncanonical Wnt/Planar Cell Polarity Signaling", Circulation Research, Jan. 6, 2012, 30 pages, vol. 110, © 2011 American Heart Association, Inc.; DOI: 10.1161/CIRCRESAHA.111.250936.

Ohlmann, A. et al., "Norrin: Molecular and functional properties of an angiogenic and neuroprotective growth factor", Progress in Retinal and Eye Research, 2012, pp. 243-257, vol. 31, © 2012 Elsevier Ltd.1 DOI: 10.1016/j.preteyeres.2012.02.002.

Luissint, A-C. et al., "Tight junctions at the blood brain barrier: physiological architecture and disease-associated dysregulation", Fluids and Barriers of the CNS, 2012, pp. 1-12, vol. 9, No. 23, © 2012 Luissint et al.

Wang, Y. et al., "Norrin/Frizzled4 Signaling in Retinal Vascular Development and Blood Brain Barrier Plasticity", Cell, Dec. 7, 2012, pp. 1332-1344, vol. 151, © 2012 Elsevier Inc; DOI: 10.1016/j.cell.2012.10.042.

Koo, N.K. et al., "Resolution of Macular Edema after Systemic Treatment with Furosemide", Korean J. Ophthalmol., 2012, pp. 312-315, vol. 26, No. 4, © 2012 The Korean Ophthalmological Society; DOI: 10.3341/kjo.2012.26.4.312.

Romero-Aroca, P., "Current status in diabetic macular edema treatments", World Journal of Diabetes, Oct. 15, 2013, pp. 165-169, vol. 4, No. 5, © 2013 Baishideng; DOI: 10.4239/wjd.v4.i5.165.

Ke, J. et al., "Structure and function of Norrin in assembly and activation of a Frizzled 4—Lrp5/6 complex", Genes and Development, 2013, pp. 2305-2319, vol. 27, © 2013 Cold Spring Harbor Laboratory Press; DOI: 10.1101/gad.228544.113.

Lee, H. et al., "Norrin expression in endothelial cells in the developing mouse retina", Acta Histochemica, 2013, pp. 447-451, vol. 115, © 2012 Elsevier GmbH; DOI: 10.1016/j.acthis.2012.10.008.

(56) References Cited

OTHER PUBLICATIONS

Weidemann, A.K. et al., "Vascular endothelial growth factor inhibitors: investigational therapies for the treatment of psoriasis", Clinical, Cosmetic and Investigational Dermatology, Sep. 25, 2013, pp. 233-244, vol. 6, © 2013 Weidmann et al.; DOI: 10.2147/CCID.S35312.

Braunger, B.M. et al., "Constitutive overexpression of Norrin activates Wnt/β-catenin and endothelin-2 signaling to protect photoreceptors from light damage", Neurobiology of Disease, 2013, pp. 1-12, vol. 50, © 2012 Elsevier Inc.; DOI: 10.1016/j.nbd.2012.09.008.

Planutis, K. et al., "A novel signaling pathway regulates colon cancer angiogenesis through Norrin", Scientific Reports, Jul. 9, 2014, pp. 1-5, vol. 4, No. 5630, DOI: 10.1038/srep05630.

Zhou, Y. et al., "Canonical WNT signaling components in vascular development and barrier formation", The Journal of Clinical Investigation, Sep. 2014, pp. 3825-3846, vol. 124, No. 9, DOI: 10.1172/JCI76431.

Daily, W. et al., "Norrin Increases Vessel Integrity upon VEGF Induced Permeability", ARVO Annual Meeting Abstract, Investigative Ophthalmology & Visual Science, Apr. 2014, p. 5400, vol. 55, No. 13, © 2014 The Association for Research in Vision and Ophthalmology, Inc.

Tang, M. et al., norrin precursor [*Homo sapiens*], NCBI, 2014, 3 pages, GenBank accession No. NP_000257.1.

Chen, Y. et al., "Norrin protected Blood Brain Barrier via Frizzled 4/β-catenin Pathway after Subarachnoid Hemorrhage in Rats", Stroke, Author manuscript available in PMC Feb. 1, 2016, Published in final edited form Feb. 2015, pp. 529-536, vol. 46, No. 2; DOI: 10.1161/STROKEAHA.114.007265.

Chen, Y. et al., Response to Letter regarding Article, "Norrin Protected Blood-Brain Barrier via Frizzled-4/β-catenin Pathway after Subarachnoid Hemorrhage in Rats", Stroke, Author manuscript available in PMC Apr. 1, 2016, Published in final edited form Apr. 2015, 2 pages, vol. 46(4): e91; DOI: 10.1161/STROKEAHA.115.008779.

International Search Report dated Sep. 9, 2016 for International Application No. PCT/US2016/036402 filed Jun. 8, 2016.

International Search Report dated Sep. 12, 2016 for International Application No. PCT/US2016/036438 filed Jun. 8, 2016.

Supplementary European Search Report dated Dec. 19, 2018 for European Application No. 16808183 filed Jun. 8, 2016.

PRIOR ART FIG. 1

NORRIN REGULATION OF JUNCTION PROTEINS AND THE USE THEREOF TO TREAT EPITHELIAL OR ENDOTHELIAL MEMBRANE LEAKAGE INDUCED EDEMA

RELATED APPLICATIONS

This application is a continuation of U.S. Utility application Ser. No. 14/733,876 filed Jun. 8, 2015; the contents of which are hereby incorporated by reference.

FIELD OF THE INVENTION

The present invention is directed generally to methods of regulating cadherin and claudin gene expression in a body tissue by applying such tissue norrin protein, and in particular, to produce additional cellular production of cadherin and claudin-5 to limit edema associated with compromised Tight Junctions.

BACKGROUND OF THE INVENTION

Various inflammatory diseases are characterized by leakage induced edema. On a cellular level, this edema is associated with the junctions between epithelial or endothelial cells being compromised. One such mechanism related to this type of inflammation is ischemic tissue compensating for a lack of oxygen & nutrients by excessively up-regulating cytokines involved in permeability. The over-expression of vascular endothelial growth factor (VEGF) causes an increase in vessel permeability due to depletion of cell-to-cell adhesion molecules such as VE-cadherin and claudin-5. Crohn's disease and inflammatory bowel disease have been shown to progress through a failed tight junction mechanism. (J D Schulzke et al. *Ann N Y Acad Sci.* 2009 May; 1165:294-300. doi: 10.1111).

Endothelial tight junctions are found in a variety of tissues including blood vessels and the brain, the endothelial lining of the vessel wall forms a controlled permeable barrier, which is located at the interface between the vascular and the perivascular compartments. Although the endothelium acts as an efficient barrier that strictly separates the two compartments, it may also act as a permeable filter which allows selective exchange of solutes and water between the luminal and abluminal sides of the barrier. A disruption of the equilibrium function through tight junction failure leads to a variety of inflammatory conditions of the vasculature, lymphatic system, and brain. While such conditions are routinely treated with steroidal or non-steroidal anti-inflammatories, such existing therapies have limitations in terms of efficacy, as well as side-effects.

Additionally, many cancers progress only through angiogenesis that is promulgated by vascular endothelial growth factor (VEGF) and metastasis of tumors necessarily requires the loosening of junctions between cancerous cells to allow cells to become circulatory. While not causative of cancer, this mechanism seems to be important in proliferation.

The epithelial and endothelial layers are sites of exchange as well as barriers, for the transit of ions and molecules between tissues and the circulatory system of the organism. Complexes between adjacent epithelial and endothelial cells include Tight Junctions and Adherens junctions. Vertebrate epithelial and endothelial cells exhibit Tight Junctions that lie apical to Adherens Junctions. Tight Junctions have an organizing role in epithelial and endothelial polarization and establish an apico-lateral barrier to the diffusion of solutes through the intracellular space (gate function). Tight junctions also restrict the movement of lipids and membrane proteins between the apical and the basolateral membrane (fence function). Tight Junctions are highly ordered membrane contact sites, comprising a network of intra-membrane fibrils. Tight Junctions include transmembrane proteins, including occludin, claudin-5, and junctional adhesion molecules (JAMs), and a number of cytoplasmic peripheral proteins. These are shown schematically in prior art FIG. 1. While the transmembrane proteins mediate cell-cell adhesion, the cytosolic tight junction plaque contains various types of proteins (e.g. PDZ proteins, such as the ZO (Zona Occludens) family) that link tight junction transmembrane proteins to the underlying cytoskeleton. These adapters also recruit regulatory proteins, such as protein kinases, phosphatases, small GTPases and transcription factors, to the tight junctions. As a result, structural (Actin and Spectrin) and regulatory (Actin-binding proteins, GTPases and kinases) proteins are juxtaposed with transmembrane proteins. This protein scaffolding facilitates the assembly of highly ordered structures, such as junctional complexes or signaling patches that regulate epithelial cell polarity, proliferation and differentiation.

Tight Junctions are located at the uppermost portion of the lateral plasma membrane, where the integral membrane proteins like claudins appear to be involved in the homophilic and/or heterophilic interactions implicated in firm adhesions. Claudins have four hydrophobic transmembrane domains and two extracellular loops. The extracellular loops, whose sequences are distinct in different claudins, contribute to the formation not only of tight junction strands but also of ion-selective channels. Claudin-5 is important in endothelial and epithelial cell junctions. In general, tight junction strands are linear co-polymers of occludin, claudin-5, and JAMs that attract cytoplasmic proteins containing PDZ domains (OZ) have high affinity for the C-terminal sequences of these proteins.

Tight Junctions and Adherens Junctions are functionally and structurally linked, endothelial VE-cadherin associated with Adherens Junctions upregulates the gene encoding the Tight Junction adhesive protein claudin-5 and a similar structure is found in epithelial cells with E-cadherin in place of VE-cadherin. This effect requires the release of the inhibitory activity of forkhead box factor FoxO1 to suppress proteasome activity. Vascular endothelial (VE)-cadherin acts by inducing the phosphorylation of FoxO1 through Akt activation and by limiting the translocation of beta-catenin to the nucleus. (Taddei et al. *Nat Cell Biol.* 2008 August; 10(8):923-34. doi: 10.1038/ncb1752. Epub 2008 Jul. 6). Polycystin-1 (PDK-1) is a membrane protein localized to Adherens Junctions in a complex containing beta-catenins, that is mediated by P13K.

VEGF induces vascular permeability through induction of the rapid endocytosis of a key endothelial and epithelial cell adhesion molecule, Cadherin, thereby disrupting the barrier function. This process is initiated by the activation of the small GTPase, Rac by VEGFR through the Src-dependent phosphorylation of Vav2 (not shown), a guanine nucleotide-exchange factor. Rac activation, in turn, promotes the p21-activated kinase (PAK)-mediated phosphorylation of a highly conserved motif within the intracellular tail of Cadherin. This results in the disassembly of intercellular junctions. (Gavard et al., *Nat Cell Biol.* 2006 November; 8(11): 1223-34. Epub 2006 Oct. 22).

In a normally functioning exemplary epithelial cell shown in the left panel of FIG. 1 with an intact Tight Junction, VEGF is not bound to its corresponding receptor VEGFR, and claudin-5 is expressed normally in the nucleus from the encoding claudin-5 gene and processed by the endoplasmic reticulum. The occuludin, claudin-5, and and JAM together form a functioning Tight Junction, and Cadherin forms and organized Adherens Junction.

In contrast, with VEGF binding to VEGFR, as shown in the right panel of FIG. 1, the Src/Rac/Pak complex acts on beta-catenins to destabilize the Adherens Junction. The resultant cascade is believed to disrupt claudin-5 expression and assembly resulting in a loss of Tight Junction structure.

Norrin is a ligand for the Frizzled receptor subtype 4 (Fz4). Norrin binds Fz4 with nanomolar affinity (Xu, et al, *Cell*, 2004; 116:883-895; Clevers, *Curr Biol*, 2004; 14:R436-437; Nich, *Dev Cell*, 2004; 6:453-454). Norrin interaction with Fz4 is dependent on the cell surface receptor LRP5. (Xu, 2004). Frizzled receptors are coupled to the β-catenin canonical signaling pathway. The inactivation of glycogen synthase kinase (GSK) 3β and Axin through frizzled receptor binding stabilizes β-catenin, which subsequently accumulates in the cell nucleus and activates the transduction of target genes that are crucial in the G1-S-phase transition, such as cyclin D1 or c-Myc. (Willert et al., *Curr Opin Genet Dev*, 1998; 8:95-102). Suppression of norrin activity has been shown to preclude angiogenesis associated with ocular disease (US 2010/0129375).

Thus, there exists a need for a method to treat edema associated with endothelial and epithelial membrane leakage. There further exists a need for a method to treat clinical disorders associated with endothelial and epithelial cell membrane failure edema. There also exists a need for a method to produce cadherin and clatidin-5. The present invention is directed to these, as well as other, important needs in the art.

SUMMARY OF THE INVENTION

A method of tightening inter-cellular junctions in endothelial and epithelial cells includes exposing the cells to norrin. Upon sufficient contact time, for norrin to selectively up-regulate gene expression of cadherin or claudin-5 in the cells, the inter-cellular junctions are tightened. The method is effective in vivo in a human subject. Norrin is readily administered by injection, oral administration, or topical administration.

A norrin truncate or fragment that is capable of binding a frizzled-4 receptor of a target cell can be used and afford greater solubility than native norrin. The norrin used herein can be recombinant.

BRIEF DESCRIPTION OF THE DRAWINGS

These and other aspects of the present invention be elucidated in the accompanying drawings and following detailed description of the invention.

DETAILED DESCRIPTION OF THE INVENTION

The present invention has utility as a method to make limit inter-cellular leakage between endothelial and epithelial cells in a subject. As a result, a clinical disorder in which edema occurs based on leakage of the Adherens Junctions or Tight Junctions in endothelial and epithelial cells is readily treated. The present invention is particularly well-suited for usage in response to the compromise of the blood-brain barrier (BBB), or the blood-intestinal barrier (BIB). A method is also provided for the production of cadherin and claudin-5. In a particular application, inflammation associated with Crohn's disease is reduced; a condition currently with limited clinical treatments. The invention will be described in detail below. Those skilled in the art will appreciate that the description given herein is for exemplary purposes only and is not intended in any way to limit the scope of the invention.

Figure 1:
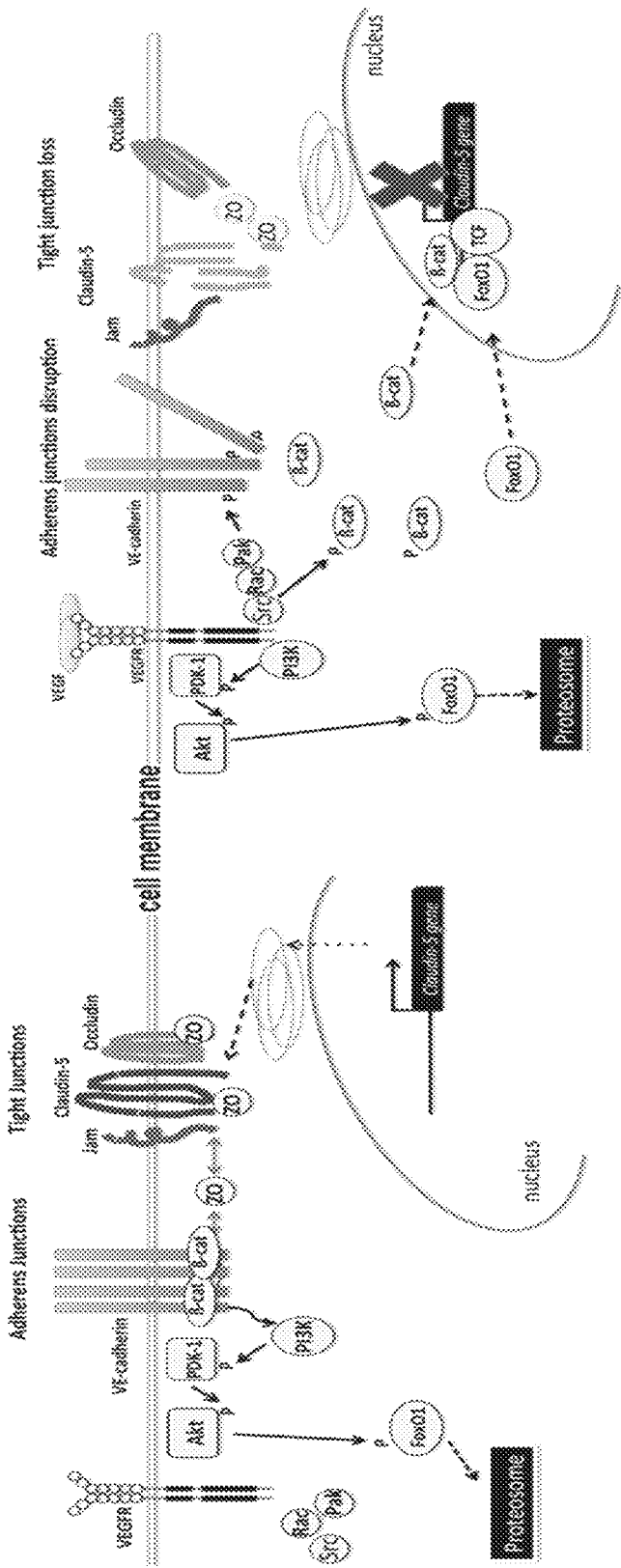
FIG. 1 are prior art schematics of a cell having intact cell junctions (left panel) and weakened or disrupted cell junctions (right panel), showing the function of VEGF in changing the pathway of certain highlighted cellular pathways.
Figure 2:
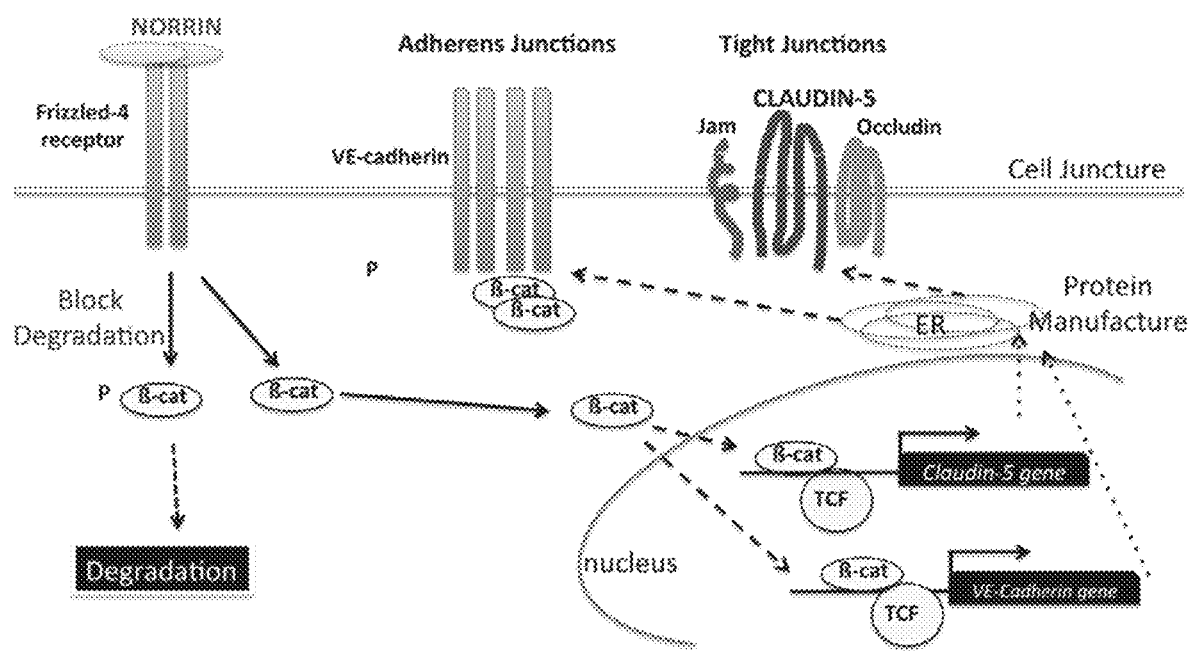
FIG. 2 is a schematic of a possible pathway for the effectiveness of the present invention to induce cellular expression of VE-cadherin and claudin-5.

Without intending to be hound to a particular theory of operation, the binding of norrin protein to a frizzled-4 receptor of an endothelial or epithelial cell limits degradation of beta-catetin, that then accumulates and localizes to the cell nucleus and subsequently induce a cellular response via gene transduction alongside the TCF/LEF (T-cell factor/lymphoid enhancing factor). Claudin-5 and cadherin genes are then transcribed and the corresponding proteins manufactured via the endoplasmic reticulum. The resulting proteins repair a compromised cell juncture. This is shown schematically in FIG. 2. The claudin-5 and cadherin proteins are also subject to harvest or usage in experimental studies in certain embodiments of the invention.

The following definitions are used herein with respect to the understanding of the present invention.

"Administering" is defined herein as a means of providing norrin protein or a composition containing norrin to a subject endothelial or epithelial cells with compromised junctions. Such an administration can be by any route including, without limitation, oral, transdermal (e.g. oral mucosa), by injection (e.g., subcutaneous, intravenous, parenterally, intraperitoneally,), by inhalation (e.g., oral or nasal), or topical (e.g., eyedrops, cream, etc.). Pharmaceutical preparations are, of course, given by forms suitable for each administration route.

By "alteration" is meant a change (increase or decrease) in the expression levels or activity of a gene or polypeptide as detected by standard art known methods such as those described herein. As used herein, an alteration includes at least a 10% change in expression levels, preferably a 25% change, more preferably a 40% change, and most preferably a 50% or greater change in expression levels.

By "analog" is meant a molecule that is not identical, but has analogous functional or structural features to norrin protein. For example, a polypeptide analog retains the biological activity of a corresponding naturally-occurring norrin, while having certain biochemical modifications that enhance the analog's function relative to a naturally occurring polypeptide. Such biochemical modifications could increase the analog's protease resistance, solubility, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "control" is meant a standard or reference status.

"Cadherin" is meant to refer to vascular endothelial cadherin with reference to endothelial cells (VE-cadherin) and epithelial cadherin (E-cadherin) with reference to epithelial cells.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "fragment" is meant a portion of norrin. This portion contains, preferably, at least 40%, 50%, 60%, 70%, 80%, or 90% of the entire length of the 133 amino acid residues of the native human norrin polypeptide. A fragment may contain 40, 50, 60, 70, 80, 90, 100, 110, 120, 130 or even the complete 133 amino acids.

By "truncate" is meant to include a fragment of norrin that has a polypeptide terminus cleavage of the norrin protein of up 40 amino acid residues.

By an "isolated polypeptide" is meant a polypeptide analog of norrin that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

Norrin is meant to define a polypeptide or fragment thereof having at least about 85% amino acid identity to NCBI Accession No. NP_000257.1, as shown below, and having the ability to bind the frizzled-4 receptor of retinal epithelial cells. gi|45577891|ref|NP_000257.1| norrin precursor [*Homo sapiens*]

(SEQ ID NO. 1)
MRKHVLAASFSMLSLLVIMGDTDSKTDSSFIMDSDPRRCMRHHYVDSISH

PLYKCSSKMVLLARCEGHCSQASRSEPLVSFSTVLKQPFRSSCHCCRPQT

SKLKALRLRCSGGMRLTATYRYILSCHCEECNS

As used herein, "obtaining" as in "obtaining an agent" includes synthesizing, purchasing, or otherwise acquiring the agent.

The term "patient" or "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

As used herein, the terms "treat," "treated," "treating," "treatment," and the like refer to reducing or ameliorating a disorder and/or symptoms associated therewith BRB compromise.

Typically a therapeutically effective dosage should produce a serum concentration of compound of from about 0.1 ng/ml to about 50-100 µg/ml.

Unless specifically stated or obvious from context, as used herein, the term "or" is understood to be inclusive. Unless specifically stated or obvious from context, as used herein, the terms "a," "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Norrin is a 133 amino acid long protein that is secreted into the extracellular space. Two primary domains define the general norrin protein structure: a signal peptide directs localization of the molecule; and a cysteine-knot motif provides the tertiary confirmation required for frizzled-4 receptor binding. (Meitinger, T, et al, Nat Genet, 1993; 5:376-380; Berger, W, et al, Hum Mol Genet, 1996; 5:51-59). Truncates and fragments of norrin that retain the ability to bind frizzled-4 receptor are operative herein. In some inventive embodiments a truncate or fragment of norrin retains the cysteine-knot motif.

The importance of the cysteine knot-motif is highlighted by computer modeling that demonstrates the requirement of disulfide bonds between the cysteine residues in forming the structural confirmation of norrin. However, mutations in regions other than the cysteine knot-motif produce incomplete protein folding and result in familial exudative vitreoretinopathy (FEVR) and related vitreoretinopathies.

In certain inventive embodiments a 24 residue N-terminus truncate of norrin, with the following amino acid sequence:

```
                                                (SEQ ID NO: 2)
KTDSSFIMDSDPRRCMRHHYVDSISHPLYKCSSKMVLLARCEGHCSQASR

SEPLVSFSTVLKQPFRSSCHCCRPQTSKLKALRLRCSGGMRLTATYRYIL

SCHCEECNS (Accession # Q00604)
```

It has been found that some fragments and truncations such as SEQ ID NO: 2 have improved solubility compared to norrin.

The invention further embraces variants and equivalents which are substantially homologous to norrin and still retain the ability to selectively bind the frizzled-4 receptor. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid.

Figure 6:
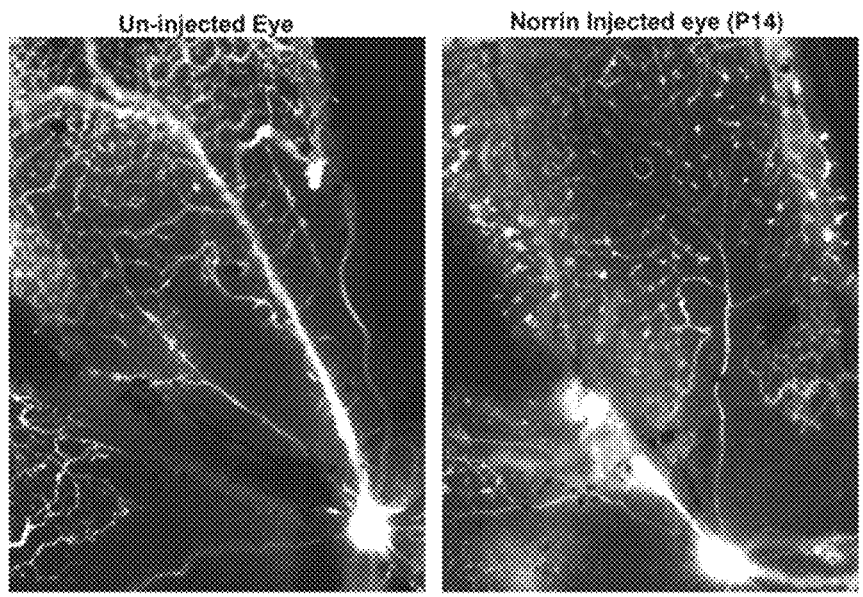
FIG. 6 are retinal micrographs depicting Evans Blue leakage in eyes of an oxygen induced retinopathy (OIR) model of a mouse, with an uninjected eye (left panel) and an eye injected with norrin (right panel), the images taken 3 days after norrin injection, where bright (white) is indicative of vascular leakage and the injected eye shows preservation of the capillary network.

The norrin of the present invention can be recombinant norrin, natural norrin, or synthetic norrin retaining frizzled-4 binding properties. It will be recognized in the art that some amino acid sequences of the invention can be varied without significant effect of the structure or function of the protein. Thus, the invention further includes variations of the norrin which show substantial activity; such mutants include deletions, insertions, inversions, repeats, and type substitutions. Norrin mutants operable herein illustratively include amino acid substitutions relative to SEQ ID NO: 1 of R64E. Optionally the biologically active peptide is a multiple mutant relative to SEQ ID NO: 1: T26A, S28A, S29A; P36A, R37A, R38A; Y120A, R121A, Y122A; or H127A, E129A, E130A; or combinations thereof. Any amino acid mutated in a multiple mutation is operable as a single mutation. Other sequence mutations operative herein are illustrated in FIG. 6A of Smallwood, P M, et al, J Biol Chem, 2007: 282:4057-4068 or Ke, J et al. Genes& Dev. 2013: 27: 2305-2319. It is appreciated that other mutations at different amino acid sites are similarly operable. It is further appreciated that mutation of the conserved amino acid at any particular site is preferably mutated to glycine or alanine. It is further appreciated that mutation to any neutrally charged, charged, hydrophobic, hydrophilic, synthetic, non-natural, non-human, or other amino acid is similarly operable.

Modifications and changes are optionally made in the structure (primary, secondary, or tertiary) of the Norrin protein which are encompassed within the inventive compound that may or may not result in a molecule having similar characteristics to the exemplary polypeptides disclosed herein. It is appreciated that changes in conserved amino acid bases are most likely to impact the activity of the resultant protein. However, it is further appreciated that changes in amino acids operable for receptor interaction, resistance or promotion of protein degradation, intracellular or extracellular trafficking, secretion, protein-protein interaction, post-translational modification such as glycosylation, phosphorylation, sulfation, and the like, may result in increased or decreased activity of an inventive compound while retaining some ability to alter or maintain a physiological activity. Certain amino acid substitutions for other amino acids in a sequence are known to occur without appreciable loss of activity.

In making such changes, the hydropathic index of amino acids are considered. According to the present invention, certain amino acids can be substituted for other amino acids having a similar hydropathic index and still result in a polypeptide with similar biological activity. Each amino acid is assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Without intending to be limited to a particular theory, it is believed that the relative hydropathic character of the amino acid determines the secondary structure of the resultant polypeptide, which in turn defines the interaction of the polypeptide with other molecules. It is known in the art that an amino acid can be substituted by another amino acid having a similar hydropathic index and still obtain a functionally equivalent polypeptide. In such changes, the substitution of amino acids whose hydropathic indices are within ±.2 is preferred, those within .±.1 are particularly preferred, and those within .±.0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu).

The norrin and analogs can be further modified to contain additional chemical moieties not normally part of the protein. Those derivatized moieties can improve the solubility, the biological half-life absorption of the protein, or binding affinity. The moieties can also reduce or eliminate any desirable side effects of the proteins and the like. An overview for those moieties can be found in Remington's Pharmaceutical Sciences, 20th ed., Mack Publishing Co., Easton, Pa. (2000).

The isolated norrin described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. (Zoeller et al., Proc. Nat'l. Acad. Sci. USA 81:5662-5066 (1984) and U.S. Pat. No. 4,588,585).

According to the present invention, the Tight Junctions and Adherens Junctions of endothelial or epithelial cell with compromised junctions are exposed to a dosage of norrin, a truncate or fragment thereof. After norrin exposure the resulting cells have demonstrably higher levels of cellular junction claudin-5 and Cadherins. The present invention thus reverses the effects of cytokines including VEGF on endothelial or epithelial cells. Edema with compromised retinal or choroidal endothelial or epithelial barrier junctions are thereby reduced.

Norrin truncate of SEQ ID NO: 2 is observed to be effective in increasing cellular junction levels of claudin-5 and Cadherins at concentrations of 10 to 1000 ng/ml.

The present invention is also directed to pharmaceutical compositions comprising an effective amount of norrin alone or in combination with a pharmaceutically acceptable carrier, excipient or additive. Particularly favored derivatives are those that increase the bioavailability of norrin administered to a mammal (e.g., by allowing norrin to be more readily absorbed into the blood) or which enhance delivery of the norrin to a biological compartment (e.g., the retina) relative to the native protein.

To prepare the pharmaceutical compositions according to the present invention, a therapeutically effective amount of norrin is preferably intimately admixed with a pharmaceutically acceptable carrier according to conventional pharmaceutical compounding techniques to produce a dose. A carrier may take a wide variety of forms depending on the form of preparation desired for administration, e.g. oral, topical or parenteral, including gels, creams ointments, lotions and time released implantable preparations, among numerous others.

Norrin is also administered with an adjunct therapeutic such as an anti-VEGF agent. An anti-VEGF agent operative illustratively includes bevacizumab, ranibizumab small molecules that inhibit the tyrosine kinases stimulated by VEGF such as lapatinib, sunitinib, sorafenib, axitinib, pazopanib, or a combination thereof. A medicament of an anti-VEGF agent and norrin in a suitable carrier is also provided. The combination therapy is found to more effective than a conventional anti-VEGF agent. By way of example, anti-VEGF intraocular injections are effective in about 78% of subjects with retinal edema secondary to diabetes; whereas a combination therapy with norrin increases this efficacy to greater than 85%. Without intending to be bound to a particular theory, the binding anti-VEGF to a VEGF receptor is less than complete owing to factors such as kinetics, and receptor variation between subjects and as a result an inflammatory cascade can still be initiated with anti-VEGF agents. Norrin in improving inter-cellular junctions compensates for such VEGF activity occurring in the presence of anti-VEGF agents.

A solution carrier suitable for injection is particularly advantageous for treating retinal edema and wet macular degeneration.

Solutions or suspensions used for parenteral, intradermal, subcutaneous, or topical application can include the following components: a sterilediluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediamic acid; buffers such as acetates, citrates or phosphates and agents for the adjustment of tonicity such as sodium chloride or dextrose.

Administration in the form of a liquid oral preparation uses a carrier in a form such as suspensions, elixirs and solutions, suitable carriers and additives including water, glycols, oils, alcohols, flavoring agents, preservatives, coloring agents and the like may be used. For solid oral administration, preparations are provided in a form such as powders, tablets, capsules, and for solid preparations such as suppositories, suitable carriers and additives including starches, sugar carriers, such as dextrose, mannitol, lactose and related carriers, diluents, granulating agents, lubricants, binders, or disintegrating agents. If desired, the tablets or capsules may be enteric-coated or sustained release by standard techniques. Norrin is provided in a solid dose is lyophilized form or in pelletized solution droplets.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, poly anhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

Formulations suitable for topical administration to the skin may be presented as ointments, creams, gels and pastes including the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier will usually comprise sterile water or aqueous sodium chloride solution, though other ingredients including those which aid dispersion may be included. Of course, where sterile water is to be used and maintained as sterile, the norrin and carriers must also be sterilized. Injectable suspensions may also be prepared, in which case appropriate liquid carriers, suspending agents and the like may be employed.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include topical, parenteral, intramuscular, intravenous, sub-cutaneous, intrachoroidal or, transdermal (which may include a penetration enhancement agent).

Application of the subject therapeutics may be local, so as to be administered at the site of interest. Various techniques can be used for providing the subject norrin at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject norrin, the subject norrin may be painted onto the organ, or may be applied in any convenient way.

Norrin may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment. More specifically, the norrin is administered through a intralymphatic or intrathecal device suitable for direct implantation into a lymphatic vessel or the brain, respectively. Such devices of the present invention are surprisingly found to provide sustained controlled release of various norrin to treat the eye without risk of detrimental local and systemic side effects. See. e.g., U.S. Pat. Nos. 5,378,475; 5,773,019; 6,001,386; 6,217,895, 6,375,972 and 6,756,058.

Other methods of delivery of norrin include: injecting the system or surgically implanting the system, a sustained release drug delivery system, and a method for providing controlled and sustained administration of the norrin in a desired local or systemic physiological or pharmacological effect comprising surgically implanting a sustained release drug delivery system at a desired location.

Examples include, but are not limited to the following: a sustained release drug delivery system comprising an inner reservoir containing norrin, an inner tube impermeable to the passage of the agent, the inner tube having first and second ends and covering at least a portion of the inner reservoir, the inner tube sized and formed of a material so that the inner tube is capable of supporting own weight, an impermeable member positioned at the inner tube first end, the impermeable member preventing passage of the agent out of the reservoir through the inner tube first end, and a permeable member positioned at the inner tube second end, the permeable member allowing diffusion of the agent out of the reservoir through the inner tube second end. A method for administering norrin to a segment of portion of the brain, includes implanting a sustained release device to deliver norrin to the region of the brain, or an implantable, sustained release device for administering a compound of the invention to a portion of the brain; a sustained release drug delivery device includes a) a drug core containing norrin; b) at least one unitary cup essentially impermeable to the passage of the agent that surrounds and defines an internal compartment to accept the drug core, the unitary cup including an open top end with at least one recessed groove around at least some portion of the open top end of the unitary cup; c) a permeable plug which is permeable to the passage of norrin, the permeable plug is positioned at the open top end of the unitary cup wherein the groove interacts with the permeable plug holding it in position and closing the open top end, the permeable plug allowing passage of the agent out of the drug core, through the permeable plug, and out the open top end of the unitary cup. A sustained release norrin delivery device includes an inner core norrin having a desired solubility and a polymer coating layer, the polymer layer being permeable to norrin, wherein the polymer coating layer completely covers the inner core. It is appreciated that sustained release is well suited to delay metastasis in a variety of cancers including colorectal and lymphatic.

Norrin may be administered as microspheres. For example, norrin may be purchased from R&D Systems, Minneapolis, Minn., or cloned, expressed and purified is loaded into biodegradable microspheres substantially as described by Jiang, C, et al, *Mol. Vis.,* 2007; 13:178:3-92 spontaneous emulsification technique of Fu, K, et al, *J. Pharm. Sci.,* 2003; 92:1582-91. Microspheres are synthesized and loaded by dissolving 200 mg of 50:50 poly (lactide-co-glycolic acid) (PLGA) in 5 ml of 4:1 volume ratio trifluoroethanol:dichloromethane supplemented with 8 mg magnesium hydroxide to minimize protein aggregation during encapsulation. 10 μg norrin may be reconstituted in 300 μl 7 mg bovine serum albumin (BSA) and 100 mg docusate sodium (Sigma-Aldrich, St. Louis, Mo.) dissolved in 3 ml PBS. The solution may be vortexed and poured into 200 ml of 1% (w/v) polyvinyl alcohol (PVA, 88% hydrolyzed) with gentle stirring. Microspheres may be hardened by stirring for three hours, collected by centrifugation, and washed three times to remove residual PVA. If the microspheres are not to be immediately injected they are rapidly frozen in liquid nitrogen, lyophilized for 72 h, and stored in a dessicator at −20° C. Norrin containing microspheres exhibit average diameters of 8μm as determined by a particle size. Norrin may also be administered by intravitreal injection. For example, norrin in solution, may be packaged into microspheres as described above, or expressed in cells, or in purified form in solution may be exposed to the brain or lymphatic system by intrathecal or intralymphatic injection. Such injection may be performed under general anesthesia using an operating microscope (Moller-Wedel GmbH, Wedel, Germany) using beveled glass micro-needles with an outer diameter of approximately 100 μm Microsphere suspensions are prepared in PBS at 2 and 10% (w/v) and briefly vortexed immediately before injection to ensure a uniform dispersion. A 30-gauge hypodermic needle may be used to perforate the intervening tissues. Five microliters of test sample is optionally injected by way of this passage into the luminal space using a 50 μl Hamilton. Syringe (Hamilton Co, Reno, Nev.). To ensure adequate delivery and prevent shock the needle is held in place for one min after the injection is completed and subsequently withdrawn slowly. In addition, paracentesis may be simultaneously performed to relieve pressure and thereby prevent reflux.

Norrin may also be administered by delivery by a controlled release delivery system. An implantable controlled release delivery system is described in U.S. Patent Application Publication 2005/0281861 and is packaged into such as system at 100 μg per final formulated capsule. For example, a norrin containing drug delivery systems may be implanted using forceps or a trocar after making a 2-3 mm incision in the sclera. The removal of the device after the placement of the system can result in a self-sealing opening. One example of a device that is used to insert the implants is disclosed in U.S. Patent Application Publication No. 2004/0054374 which is incorporated herein by reference. The location of the system may influence the concentration gradients of therapeutic component or drug surrounding the element, and thus influence the release rates (e.g., an element placed closer to the edge of the vitreous may result in a slower release rate).

Preferred unit dosage formulations are those containing a daily dose or unit, daily sub-dose, as hereinabove recited, or an appropriate fraction thereof, of the administered ingredient.

The dosage regimen for norrin invention is based on a variety of factors, including the degree of leakage in the BBB, or BIB, the route of administration, abluminal inflammation volume, and the particular norrin employed. Thus, the dosage regimen may vary widely, but can be determined routinely using standard methods.

In certain embodiments, norrin is administered once daily; in other embodiments, norrin is administered twice daily; in yet other embodiments, norrin is administered once every two days, once every three days, once every four days, once every five days, once every six days, once every seven days, once every two weeks, once every three weeks, once every tour weeks, once every two months, once every six months, or once per year. The dosing interval can be adjusted according to the needs of individual patients. For longer intervals of administration, extended release or depot formulations can be used.

Pharmaceutically acceptable carriers, excipients, or diluents illustratively include saline, buffered saline, dextrose, water, glycerol, ethanol, sterile isotonic aqueous buffer, and combinations thereof.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as PLEA, polyglactin, poly-(isobutyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), polylactic acid), poly(glycolic acid) or poly(ortho esters).

Examples of preservatives include, but are not limited to, parabens, such as methyl or propyl p-hydroxybensoate and benzalkonium chloride.

Injectable depot forms are made by forming microencapsule matrices of compound(s) of the invention in biodegradable polymers such as polylactide-polyglycolide Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Any of the above-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration the pharmaceutical compositions to the subject.

When norrin is administered as a pharmaceutical to humans or animals, norrin can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, norrin is administered in an amount sufficient to reduce or eliminate symptoms associated with edema or to inhibit metastasis in cancers.

Exemplary dose ranges include 0.00001 mg to 250 mg per day, 0.0001 mg to 100 mg per day, 1 mg to 100 mg per day, 10 mg to 100 mg per day, 1 mg to 10 mg per day, and 0.01 mg to 10 mg per day. A preferred dose of an agent is the maximum that a patient can tolerate and not develop serious or unacceptable side effects. In certain inventive embodiments, the therapeutically effective dosage produces a concentration of norrin of from about 0.1 ng/ml to about 50-100 μg/ml.

Determination of an effective amount is well within the capability of those skilled in the art, especially in light of the detailed disclosure provided herein. Generally, an efficacious or effective amount of a norrin is determined by first administering a low dose of the agent(s) and then incrementally increasing the administered dose or dosages until a desired effect (e.g., reduce or eliminate symptoms associated with retinal edema) is observed in the treated subject with minimal or acceptable toxic side effects. Applicable methods for determining an appropriate dose and dosing schedule for administration of a pharmaceutical composition of the present invention are described, for example, in Goodman and Oilman's The Pharmacological Basis of Therapeutics, Goodman et al., eds., 11th Edition, McGraw-Hill 2005, and Remington: The Science and Practice of Pharmacy, 20th and 21st Editions. Gennaro and University of the Sciences in Philadelphia, Eds., Lippencott Williams & Wilkins (2003 and 2005), each of which is hereby incorporated by reference.

The following are in vitro & in vivo examples of how norrin can overcome the endothelial cell depletion of cell-to-cell adhesion molecules and re-stabilize vessels which are for purposes of illustration, and are not intended to limit the scope of the present invention In Vitro Assays

Example 1: Immunostain of VE-Cadherin in Cells—VEGF Challenge

Human retinal microvascular endothelial cells (HRMECs) were cultured in DMEM supplemented with 10% (v/v) heat-inactivated FBS (Nichirei Biosciences Inc., Tokyo, Japan), 100 U/mL penicillin, 100 µg/mL streptomycin (Life Technologies Gibco, France. The cell cultures were incubated on collagen-coated tissue culture plates Transwell® (Corning, New York, N.Y.) in a humidified atmosphere of 5% $CO_2$ at 37° C.

HRMECs were cultured for 14 to 21 d on a Lab-Tek chamber plate (Corning). $H_2O_2$ (500 µmol/L) was administered to the basolateral side of the Transwell®. To some plates nothing was added (Control), or VEGF (100 ng/mL) or norrin truncate (SEQ ID NO: 2) (250 ng/ml) or both VEGF and norrin (100 ng/ml and 250 ng/ml, respectively) was added to the apical medium 30 min prior to $H_2O_2$ treatment. After 6 h of incubation, the cells were washed twice with cold PBS and fixed with cold acetone (Wako Pure Chemical Industries, Osaka, Japan) for 10 min. The cells were then removed from the Transwell® and mounted on slides. Next, the cells were incubated with mouse anti-human VE-cadherin at 4° C. overnight. After washing with PBS, the cells were incubated with dye-conjugated secondary antibody specific to the anti-human VE-cadherin antibody then subsequently washed in PBS. The immunofluorescence was examined and imaged using fluorescence microscopy.

Figure 3:
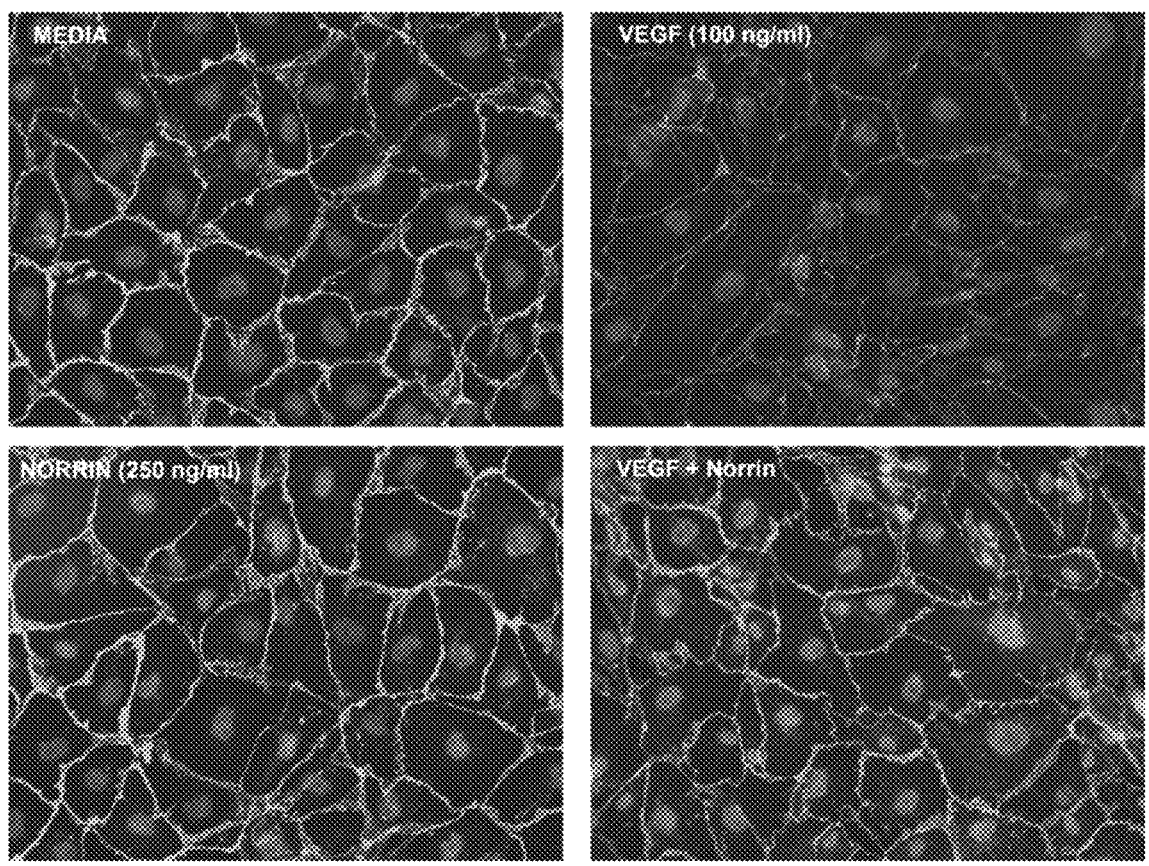
FIG. 3 are 20× magnification fluorescence micrographs of human retinal microvascular endothelial cells (HRMECs) immunostained (green at boundaries around cells) for VE-cadherin after 24 hours in media alone (upper left panel), after exposure to: VEGF (100 ng/ml of media) (upper right panel), norrin (250 ng/ml of media) (lower left panel), and both VEGF (100 ng/ml of media) and norrin (250 ng/ml of media) (lower right panel)

Under control conditions, claudin-5 are localized to cell-cell boundaries of these cells as shown in the upper left panel of FIG. 3. After addition of VEGF (upper right panel, FIG. 3) one can see a reduction in cell-cell adhesion molecules as well as a loss in the cobblestone morphology. However with the combination of VEGF and norrin (lower right panel, FIG. 3) the junction proteins and morphology were restored. The effect of norrin alone is noted (lower left panel, FIG. 3).

Example 2: Immunostain of Claudin-5 in Cells—VEGF Challenge

The process of Example 1 was repeated with mouse anti-human claudin-5 antibody at 4° C. overnight instead of anti-human VE-cadherin. After washing with PBS, the cells were incubated with dye-conjugated secondary antibody specific to the anti-human claudin 5 antibody then subsequently washed in PBS prior to being imaged using fluorescence microscopy.

Figure 4:
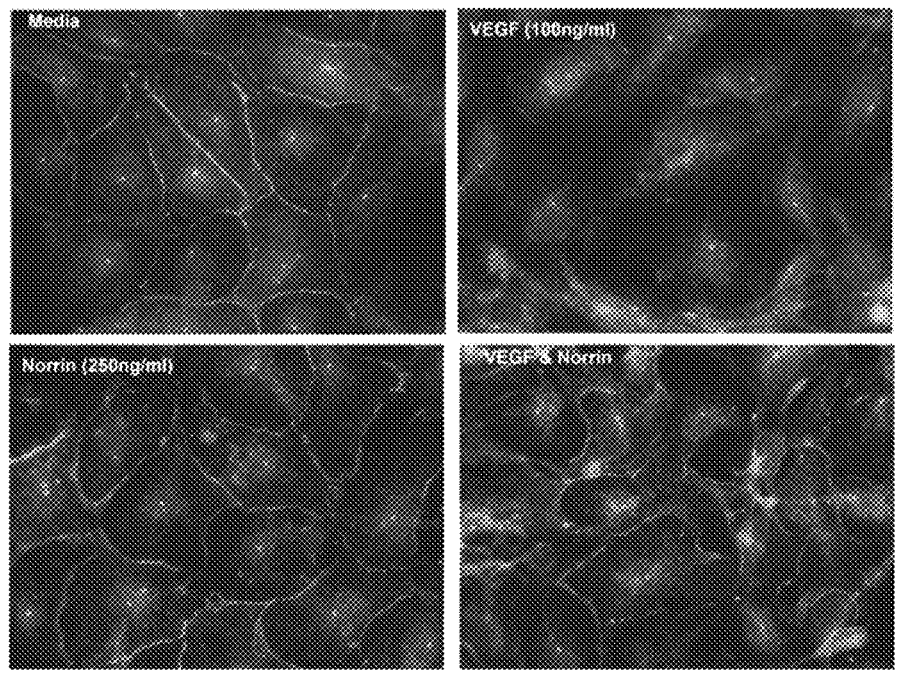
FIG. 4 are 40× magnification fluorescence micrographs of HRMECs immunostained (green at boundaries around cells) for claudin-5 after 24 hours in media alone (upper left panel), after exposure to: VEGF (100 ng/ml of media) (upper right panel), norrin (250 ng/ml of media) (lower left panel), and both VEGF (100 ng/ml of media) and norrin (250 ng/ml of media) (lower right panel)

Under control conditions, claudin-5 are localized to cell-cell boundaries of these cells as shown in the upper left panel of FIG. 4. After addition VEGF (upper right panel, FIG. 4) one can see a reduction in cell-cell adhesion molecules as well as a loss in the cobblestone morphology. However with the combination of VEGF and norrin (lower right panel, FIG. 4) the junction proteins and morphology were restored. The effect of norrin alone is noted (lower left panel, FIG. 4).

Example 3: Claudin-5 mRNA Expression in Cells—VEGF Challenge

Figure 5:
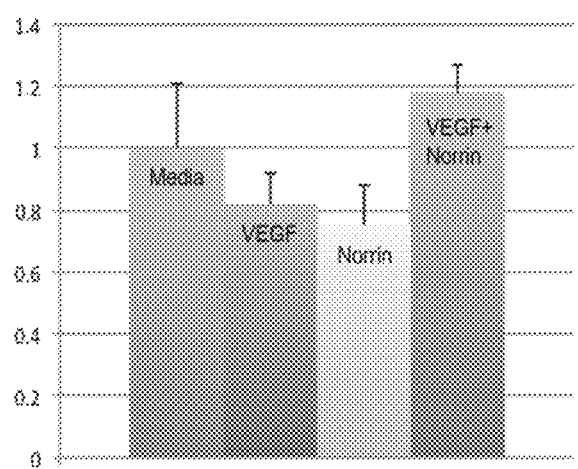
FIG. 5 is a normalized bar graph of mRNA expression of claudin-5 in a monolayer of HRMECs 24 hours after no addition, VEGF, norrin, or the combination of VEGF and norrin, showing that norrin restores claudin-5 expression.

The process of Example 4 is repeated with the replacement of TGF-beta with VEGF as the challenge agent. The amount of claudin-5 mRNA detected is shown in FIG. 5 normalized to the media only control. Norrin is observed to increase claudin-5 expression levels beyond that of the media control.

Example 4: In Vivo Assays of Vessel Leakage & Claudin-5 Stain in OIR MICE

The mouse Oxygen Induced Retinopathy Model (OIR) is used to create ischemic retina so the changes in vascular morphology and function can be assessed. Raising mice in a high oxygen environment creates areas of avascular retina. Once returned to normal oxygen environment, vessels become leaky and grow in an unregulated fashion. The amount of leakage can be visualized by systemically injecting a fluorescent dye (Evans Blue or fluoroscein) and then viewing the retina under a microscope. In OIR mice, Evans blue dye can be seen leaking from retinal vessels and claudin-5 is disrupted (left panel of FIG. 6). However, in OIR eyes injected with norrin after the OIR induction of avascular retina, Evans blue dye is confined to vessels (right panel of FIG. 6). Images were taken 4 days after norrin injection in right eye.

Example 5: Immunostain of VE-Cadherin in Vascular Cells—VEGF Challenge

The procedure of Example 1 is repeated with a culture of human microvascular endothelial cells, adult dermis (HM-VECads) in place of HRMECs. Like results are obtained to those of Example 1, demonstrating the efficacy of norrin to restore junction proteins and normal morphology.

As a person skilled in the art will recognize from the previous detailed description and from the figures and claims, modifications and changes can be made to the preferred embodiments of the invention without departing from the scope of this invention defined in the following claims.

The invention claimed is:

1. A method of treating membrane leakage edema in a living subject by tightening inter-cellular junctions in endothelial or epithelial cells to treat membrane leakage induced edema in vivo in a subject comprising:

administering by subcutaneous injection, intravenous injection, parenteral injection, or intraperitoneal injection an effective amount of an N-terminus norrin truncate having a polypeptide N-terminus cleavage relative to a native norrin protein of a maximum of 40 amino acid residues and retaining a cysteine-knot motif of the native norrin, or a norrin mutant that has at least 85% amino acid identity to SEQ. ID. NO. 1 and retains the cysteine-knot motif of the native norrin, said N-terminus norrin truncate or said norrin mutant capable of binding to the endothelial or epithelial cells defining one of: a blood vessel, a lymphatic capillary, or a blood-intestinal barrier;

administering in concert with said N-terminus norrin truncate or said norrin mutant to the endothelial or epithelial cells an effective amount an anti-VEGF agent selected from the group consisting of: bevacizumab, ranibizumab, lapatinib, sunitinib, sorafenib, axitinib, pazopanib, or a combination thereof; and allowing sufficient time for said N-terminus norrin truncate or said norrin mutant and said anti-VEGF agent in the endothelial or epithelial cells to tighten the inter-cellular junctions in the endothelial or epithelial cells for repair of the vascular leakage to treat the membrane leakage induced edema.

2. The method of claim 1, wherein the endothelial or epithelial cells are endothelial cells that define a vascular membrane.

3. The method of claim 2, wherein the endothelial or epithelial cells are endothelial cells that define a lymphatic capillary.

4. The method of claim 2, wherein the endothelial or epithelial cells are endothelial cells that define a blood-brain barrier membrane.

5. The method of claim 2, wherein the endothelial or epithelial cells are epithelial cells that define a blood-intestinal membrane.

6. The method of claim 2, wherein the administering the effective amount of said N-terminus norrin truncate or said norrin mutant step is by systemic injection.

7. The method of claim 2, wherein the administering the effective amount of said anti-VEGF agent step is by topical administration.

8. The method of claim 2, wherein said subject is human.

9. The method of claim 2, wherein said subject is one of: cow, horse, sheep, pig, goat, chicken, cat, dog, mouse, guinea pig, hamster, rabbit, or rat.

10. The method of claim 1, further comprising diagnosing edema associated with fluid leakage from a compromised cellular junction in the endothelial or epithelial cells prior to the administering the effective amount of said N-terminus norrin truncate or said norrin mutant step.

11. The method of claim 1, wherein said N-terminus norrin truncate or said norrin mutant consists of: a polypeptide of SEQ ID. NO. 2.

12. The method of claim 1, wherein said norrin is selected from the group consisting of SEQ ID. NO. 3, 5, 6, 7, 8, 9, 10, 11, 14, and 16.

13. The method of claim 1, wherein said N-terminus norrin truncate or norrin mutant is selected from the group consisting of SEQ ID. NO. 12, 13, 14, 15, 17, 18, 19, 20, and 21.

14. The method of claim 1, wherein said N-terminus norrin truncate or said norrin mutant is recombinant.

* * * * *

SEQUENCE LISTING

<160> NUMBER OF SEQ ID NOS: 21

<210> SEQ ID NO 1
<211> LENGTH: 133
<212> TYPE: PRT
<213> ORGANISM: Homo sapiens

<400> SEQUENCE: 1

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 2
<211> LENGTH: 109
<212> TYPE: PRT
<213> ORGANISM: Artificial sequence
<220> FEATURE:
<223> OTHER INFORMATION: Synthetic

<400> SEQUENCE: 2

Lys Thr Asp Ser Ser Phe Ile Met Asp Ser Asp Pro Arg Arg Cys Met
1               5                   10                  15

Arg His His Tyr Val Asp Ser Ile Ser His Pro Leu Tyr Lys Cys Ser
            20                  25                  30

Ser Lys Met Val Leu Leu Ala Arg Cys Glu Gly His Cys Ser Gln Ala
        35                  40                  45

Ser Arg Ser Glu Pro Leu Val Ser Phe Ser Thr Val Leu Lys Gln Pro
    50                  55                  60

Phe Arg Ser Ser Cys His Cys Cys Arg Pro Gln Thr Ser Lys Leu Lys
65                  70                  75                  80

Ala Leu Arg Leu Arg Cys Ser Gly Gly Met Arg Leu Thr Ala Thr Tyr
                85                  90                  95

Arg Tyr Ile Leu Ser Cys His Cys Glu Glu Cys Asn Ser
            100                 105

<210> SEQ ID NO 3
<211> LENGTH: 133
<212> TYPE: PRT
<213> ORGANISM: Artificial sequence
<220> FEATURE:
<223> OTHER INFORMATION: Synthetic

<400> SEQUENCE: 3

Met Arg Lys His Val Leu Ala Ala Ser Phe Ser Met Leu Ser Leu Leu

```
                1               5                   10                  15
Val Ile Met Gly Asp Thr Asp Ser Lys Thr Asp Ser Ser Phe Ile Met
                20                      25                      30

Asp Ser Asp Pro Arg Arg Cys Met Arg His His Tyr Val Asp Ser Ile
            35                      40                      45

Ser His Pro Leu Tyr Lys Cys Ser Ser Lys Met Val Leu Leu Ala Glu
        50                      55                      60

Cys Glu Gly His Cys Ser Gln Ala Ser Arg Ser Glu Pro Leu Val Ser
65                      70                      75                  80

Phe Ser Thr Val Leu Lys Gln Pro Phe Arg Ser Ser Cys His Cys Cys
                    85                      90                  95

Arg Pro Gln Thr Ser Lys Leu Lys Ala Leu Arg Leu Arg Cys Ser Gly
                100                     105                 110

Gly Met Arg Leu Thr Ala Thr Tyr Arg Tyr Ile Leu Ser Cys His Cys
                115                     120                 125

Glu Glu Cys Asn Ser
        130
```

<210> SEQ ID NO 4
<211> LENGTH: 133
<212> TYPE: PRT
<213> ORGANISM: Artificial sequence
<220> FEATURE:
<223> OTHER INFORMATION: Synthethic

<400> SEQUENCE: 4

```
Met Arg Lys His Val Leu Ala Ala Ser Phe Ser Met Leu Ser Leu Leu
1               5                   10                  15

Val Ile Met Gly Asp Thr Asp Ser Lys Ala Asp Ser Ser Phe Ile Met
                20                      25                      30

Asp Ser Asp Pro Arg Arg Cys Met Arg His His Tyr Val Asp Ser Ile
            35                      40                      45

Ser His Pro Leu Tyr Lys Cys Ser Ser Lys Met Val Leu Leu Ala Arg
        50                      55                      60

Cys Glu Gly His Cys Ser Gln Ala Ser Arg Ser Glu Pro Leu Val Ser
65                      70                      75                  80

Phe Ser Thr Val Leu Lys Gln Pro Phe Arg Ser Ser Cys His Cys Cys
                    85                      90                  95

Arg Pro Gln Thr Ser Lys Leu Lys Ala Leu Arg Leu Arg Cys Ser Gly
                100                     105                 110

Gly Met Arg Leu Thr Ala Thr Tyr Arg Tyr Ile Leu Ser Cys His Cys
                115                     120                 125

Glu Glu Cys Asn Ser
        130
```

<210> SEQ ID NO 5
<211> LENGTH: 133
<212> TYPE: PRT
<213> ORGANISM: Artificial sequence
<220> FEATURE:
<223> OTHER INFORMATION: Synthetic

<400> SEQUENCE: 5

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ala Ser Phe Ile Met
                20                      25                      30
```

```
Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
                100                 105                 110

Gly Met Arg Leu Thr Ala Thr Tyr Arg Tyr Ile Leu Ser Cys His Cys
                115                 120                 125

Glu Glu Cys Asn Ser
    130

<210> SEQ ID NO 6
<211> LENGTH: 133
<212> TYPE: PRT
<213> ORGANISM: Artificial sequence
<220> FEATURE:
<223> OTHER INFORMATION: Synthetic

<400> SEQUENCE: 6

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ala Phe Ile Met
                20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
                100                 105                 110

Gly Met Arg Leu Thr Ala Thr Tyr Arg Tyr Ile Leu Ser Cys His Cys
                115                 120                 125

Glu Glu Cys Asn Ser
    130

<210> SEQ ID NO 7
<211> LENGTH: 133
<212> TYPE: PRT
<213> ORGANISM: Artificial sequence
<220> FEATURE:
<223> OTHER INFORMATION: Synthetic

<400> SEQUENCE: 7

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Phe Ile Met
                20                  25                  30

Asp Ser Asp Ala Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60
```

```
Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 8
<211> LENGTH: 133
<212> TYPE: PRT
<213> ORGANISM: Artificial sequence
<220> FEATURE:
<223> OTHER INFORMATION: Synthetic

<400> SEQUENCE: 8

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Ala Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 9
<211> LENGTH: 133
<212> TYPE: PRT
<213> ORGANISM: Artificial sequence
<220> FEATURE:
<223> OTHER INFORMATION: Synthetic

<400> SEQUENCE: 9

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Ala Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
```

```
                85                  90                  95
Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
            115                 120                 125

Glu Glu Cys Asn Ser
        130

<210> SEQ ID NO 10
<211> LENGTH: 133
<212> TYPE: PRT
<213> ORGANISM: Artificial sequence
<220> FEATURE:
<223> OTHER INFORMATION: Synthetic

<400> SEQUENCE: 10

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Ala Arg Tyr Ile Leu Ser Cys His Cys
            115                 120                 125

Glu Glu Cys Asn Ser
        130

<210> SEQ ID NO 11
<211> LENGTH: 133
<212> TYPE: PRT
<213> ORGANISM: Artificial sequence
<220> FEATURE:
<223> OTHER INFORMATION: Synthetic

<400> SEQUENCE: 11

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Cys His Cys Cys
                85                  90                  95

Arg Pro Gln Thr Ser Lys Leu Lys Ala Leu Arg Leu Arg Cys Ser Gly
            100                 105                 110
```

```
Gly Met Arg Leu Thr Ala Thr Tyr Ala Tyr Ile Leu Ser Cys His Cys
        115                 120                 125

Glu Glu Cys Asn Ser
    130
```

<210> SEQ ID NO 12
<211> LENGTH: 133
<212> TYPE: PRT
<213> ORGANISM: Artificial sequence
<220> FEATURE:
<223> OTHER INFORMATION: Synthetic

<400> SEQUENCE: 12

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Ala Ile Leu Ser Cys His Cys
        115                 120                 125

Glu Glu Cys Asn Ser
    130
```

<210> SEQ ID NO 13
<211> LENGTH: 133
<212> TYPE: PRT
<213> ORGANISM: Artificial sequence
<220> FEATURE:
<223> OTHER INFORMATION: Synthetic

<400> SEQUENCE: 13

```
Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys Ala Cys
        115                 120                 125

Glu Glu Cys Asn Ser
    130
```

<210> SEQ ID NO 14
<211> LENGTH: 133
<212> TYPE: PRT
<213> ORGANISM: Artificial sequence
<220> FEATURE:
<223> OTHER INFORMATION: Synthetic

<400> SEQUENCE: 14

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Ala Glu Cys Asn Ser
    130

<210> SEQ ID NO 15
<211> LENGTH: 133
<212> TYPE: PRT
<213> ORGANISM: Artificial sequence
<220> FEATURE:
<223> OTHER INFORMATION: Synthetic

<400> SEQUENCE: 15

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Ala Cys Asn Ser
    130

<210> SEQ ID NO 16
<211> LENGTH: 133
<212> TYPE: PRT

<213> ORGANISM: Artificial sequence
<220> FEATURE:
<223> OTHER INFORMATION: Synthetic

<400> SEQUENCE: 16

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65              70                  75                  80

Phe Ser Thr Val Leu Glu Gln Pro Phe Arg Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 17
<211> LENGTH: 133
<212> TYPE: PRT
<213> ORGANISM: Artificial sequence
<220> FEATURE:
<223> OTHER INFORMATION: Synthetic

<400> SEQUENCE: 17

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
        35                  40                  45

Ser His Pro Leu Tyr Lys Cys Ser Ser Lys Met Val Leu Leu Ala Arg
    50                  55                  60

Cys Glu Gly His Cys Ser Gln Ala Ser Arg Ser Glu Pro Leu Val Ser
65              70                  75                  80

Phe Ser Thr Val Leu Lys Gln Pro Phe Glu Ser Ser Cys His Cys Cys
                85                  90                  95

Arg Pro Gln Thr Ser Lys Leu Lys Ala Leu Arg Leu Arg Cys Ser Gly
            100                 105                 110

Gly Met Arg Leu Thr Ala Thr Tyr Arg Tyr Ile Leu Ser Cys His Cys
        115                 120                 125

Glu Glu Cys Asn Ser
    130

<210> SEQ ID NO 18
<211> LENGTH: 133
<212> TYPE: PRT
<213> ORGANISM: Artificial sequence
<220> FEATURE:
<223> OTHER INFORMATION: Synthetic

<400> SEQUENCE: 18

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
                20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Cys His Cys Cys
                85                  90                  95

Glu Pro Gln Thr Ser Lys Leu Lys Ala Leu Arg Leu Arg Cys Ser Gly
                100                 105                 110

Gly Met Arg Leu Thr Ala Thr Tyr Arg Tyr Ile Leu Ser Cys His Cys
                115                 120                 125

Glu Glu Cys Asn Ser
        130

<210> SEQ ID NO 19
<211> LENGTH: 133
<212> TYPE: PRT
<213> ORGANISM: Artificial sequence
<220> FEATURE:
<223> OTHER INFORMATION: Synthetic

<400> SEQUENCE: 19

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
                20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Cys His Cys Cys
                85                  90                  95

Arg Pro Gln Thr Ser Glu Leu Lys Ala Leu Arg Leu Arg Cys Ser Gly
                100                 105                 110

Gly Met Arg Leu Thr Ala Thr Tyr Arg Tyr Ile Leu Ser Cys His Cys
                115                 120                 125

Glu Glu Cys Asn Ser
        130

<210> SEQ ID NO 20
<211> LENGTH: 133
<212> TYPE: PRT
<213> ORGANISM: Artificial sequence
<220> FEATURE:
<223> OTHER INFORMATION: Synthetic

<400> SEQUENCE: 20

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met

```
                    20                  25                  30
Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
 65                  70                  75                  80

Phe Ser Thr Val Leu Lys Gln Pro Phe Arg Ser Ser Cys His Cys Cys
                85                  90                  95

Arg Pro Gln Thr Ser Lys Leu Glu Ala Leu Arg Leu Arg Cys Ser Gly
                100                 105                 110

Gly Met Arg Leu Thr Ala Thr Tyr Arg Tyr Ile Leu Ser Cys His Cys
            115                 120                 125

Glu Glu Cys Asn Ser
        130

<210> SEQ ID NO 21
<211> LENGTH: 133
<212> TYPE: PRT
<213> ORGANISM: Artificial sequence
<220> FEATURE:
<223> OTHER INFORMATION: Synthetic

<400> SEQUENCE: 21

Met Arg Lys His Val Leu Ala Ala Ser Phe Ser Met Leu Ser Leu Leu
 1               5                  10                  15

Val Ile Met Gly Asp Thr Asp Ser Lys Thr Asp Ser Ser Phe Ile Met
            20                  25                  30

Asp Ser Asp Pro Arg Arg Cys Met Arg His His Tyr Val Asp Ser Ile
            35                  40                  45

Ser His Pro Leu Tyr Lys Cys Ser Ser Lys Met Val Leu Leu Ala Arg
        50                  55                  60

Cys Glu Gly His Cys Ser Gln Ala Ser Arg Ser Glu Pro Leu Val Ser
 65                  70                  75                  80

Phe Ser Thr Val Leu Lys Gln Pro Phe Arg Ser Ser Cys His Cys Cys
                85                  90                  95

Arg Pro Gln Thr Ser Lys Leu Lys Ala Leu Arg Leu Arg Cys Ser Gly
                100                 105                 110

Gly Met Glu Leu Thr Ala Thr Tyr Arg Tyr Ile Leu Ser Cys His Cys
            115                 120                 125

Glu Glu Cys Asn Ser
        130
```